United States Patent
Kawakubo et al.

[11] Patent Number: 5,942,505
[45] Date of Patent: Aug. 24, 1999

[54] 1-(5-ISOQUINOLINESULFONYL) HOMOPIPERAZINE HYDROCHLORIDE HYDRATES

[75] Inventors: Hiromu Kawakubo; Masaru Ohno, both of Shizuoka-ken, Japan

[73] Assignee: Asahi Kasei Kogyo Kabushiki Kaisha, Osaka, Japan

[21] Appl. No.: 08/930,910

[22] PCT Filed: Jun. 19, 1996

[86] PCT No.: PCT/JP96/01698

§ 371 Date: Oct. 14, 1997

§ 102(e) Date: Oct. 14, 1997

[87] PCT Pub. No.: WO97/02260

PCT Pub. Date: Jan. 23, 1997

[30] Foreign Application Priority Data

Jul. 3, 1995 [JP] Japan ................... 7-167460

[51] Int. Cl.⁶ .................................. C07D 401/12
[52] U.S. Cl. ........................... 514/218; 540/575
[58] Field of Search ............... 540/575; 514/218

[56] References Cited

U.S. PATENT DOCUMENTS 4,678,783  7/1987  Hidaka et al. ................ 514/218

FOREIGN PATENT DOCUMENTS

| 61-152658 | 7/1986 | Japan . |
| 2-256617 | 10/1990 | Japan . |
| 4-278094 | 10/1992 | Japan . |
| 6-80569 | 3/1994 | Japan . |
| 6-293643 | 10/1994 | Japan . |
| 7-41424 | 2/1995 | Japan . |

Primary Examiner—Richard L. Raymond
Assistant Examiner—Deepak R. Rao
Attorney, Agent, or Firm—Birch, Stewart, Kolasch & Birch, LLP

[57] ABSTRACT

Disclosed is a 1-(5-isoquinolinesulfonyl)homopiperazine hydrochloride hydrate having a water content of from 2.5 to 15.5% by weight represented by the following formula (I):

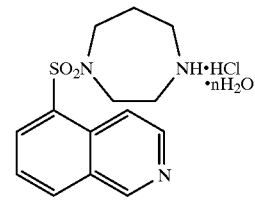

(I)

wherein n means a number in the range of from ½ to 3.

Since the 1-(5-isoquinolinesulfonyl)homopiperazine hydrochloride hydrate of the present invention has excellent shapeability as compared to a 1-(5-isoquinolinesulfonyl)homopiperazine hydrochloride anhydride, a tablet having satisfactory hardness can be obtained even with a relatively low compression pressure in a tableting process. Further, due to a reduction in the compression pressure needed for tableting, various advantages are brought about, such as improved disintegratability of the resultant tablet when the tablet is orally taken, so that good dissolution of 1-(5-isoquinolinesulfonyl)homopiperazine hydrochloride from the tablet can be achieved, as well as suppression of abrasion of the die and punch used in producing tablets by compression, and the like.

6 Claims, 7 Drawing Sheets

1-(5-ISOQUINOLINESULFONYL) HOMOPIPERAZINE HYDROCHLORIDE HYDRATES

This application is a 371 of PCT/JP96/01698 filed Jun. 19, 1996.

FIELD OF THE INVENTION

The present invention relates to a novel hydrate of 1-(5-isoquinolinesulfonyl)homopiperazine hydrochloride. More particularly, the present invention is concerned with a 1-(5-isoquinolinesulfonyl)homopiperazine hydrochloride hydrate having a water content of from 2.5 to 15.5% by weight as measured by the Karl Fischer method, represented by the following formula (I):

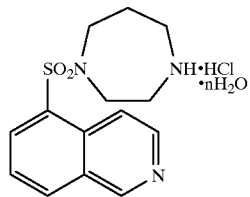

(I)

wherein n means a number in the range of from ½ to 3.

Since the 1-(5-isoquinolinesulfonyl)homopiperazine hydrochloride hydrate of the present invention has excellent shapeability as compared to a 1-(5-isoquinolinesulfonyl) homopiperazine hydrochloride anhydride, a tablet having satisfactory hardness can be obtained even with a relatively low compression pressure in a tableting process. Further, due to a reduction in the compression pressure needed for tableting, various advantages are brought about, such as improved disintegratability of the resultant tablet when the tablet is orally taken, so that good dissolution of 1-(5-isoquinolinesulfonyl)homopiperazine hydrochloride from the tablet can be achieved, as well as suppression of abrasion of the die and punch used in producing tablets by compression, and the like.

PRIOR ART 1-(5-Isoquinolinesulfonyl)homopiperazine is an isoquinolinesulfonamide compound developed by Asahi Kasei Kogyo Kabushiki Kaisha (Asahi Chemical Industries, Ltd.), Japan, and various production methods thereof are known [with respect to the synthesis methods, see Unexamined Japanese Patent Application Laid-Open Specification No. 61-227581 (corresponding to U.S. Pat. No. 4,678,783 and Examined European Patent Publication No. 0,187,371)]. 1-(5-Isoquinolinesulfonyl)homopiperazine hydrochloride [hydrochloric acid salt of the above-mentioned 1-(5-isoquinolinesulfonyl)homopiperazine] (hereinafter, frequently referred to simply as "fasudil hydrochloride") is a highly water-soluble anhydrous crystal having a melting point of 217–223° C.

1-(5-Isoquinolinesulfonyl)homopiperazine hydrochloride has excellent vasodilative activity and is clinically used for treating cerebral vasospasm (which is likely to occur after the operation of a patient suffering from subarachnoid hemorrhage), cerebral ischemic symptoms accompanying the cerebral vasospasm, and the like, wherein the above-mentioned 1-(5-Isoquinolinesulfonyl)homopiperazine hydrochloride is used in the form of an oral preparation or a parenteral preparation which is available under tradename "Eril Inj." (registered trademark for the product produced and sold by Asahi Kasei Kogyo Kabushiki Kaisha, Japan). Usually, Eril Inj. is diluted with an appropriate amount of an aqueous solution of an electrolyte or sugar and then, administered by intravenous drip in an amount of 30 mg in terms of the amount of 1-(5-isoquinolinesulfonyl)homopiperazine hydrochloride for one administration (for adult) over 30 minutes, wherein the administration is conducted twice or thrice a day. It is preferred that the administration of Eril Inj. is started in the early stage of the postoperative treatment of subarachnoid hemorrhage and conducted thrice a day for two weeks.

Conventionally, as a crystal of 1-(5-isoquinolinesulfonyl) homopiperazine hydrochloride (fasudil hydrochloride), only an anhydrous crystal has heretofore been reported, which has a water content of 1% by weight (the "% by weight" is hereinafter, frequently referred to simply as "%") or less as measured by the Karl Fischer method (all of the water contents of the crystals mentioned in the present specification are measured by the same method).

The infrared absorption (IR) spectrum of the anhydrous crystal of fasudil hydrochloride as measured by the Nujol mull method using an infrared spectrometer (all of the infrared absorption spectra mentioned in the present specification are measured in the same method) is shown in FIG. 1 of the accompanying drawings. The anhydrous crystal exhibits, in the IR spectrum thereof, characteristic peaks, i.e., a peak at approximately 1618 $cm^{-1}$ due to the skeletal stretching vibration of an isoquinoline skeleton, (ν aromatic); a peak at approximately 1588 $cm^{-1}$ due to the skeletal stretching vibration of an isoquinoline skeleton, (ν aromatic); a peak at approximately 1338 $cm^{-1}$ due to the antisymmetric stretching vibration of a sulfonamide group (ν antisymmetric $SO_2$); and a peak at approximately 1160 $cm^{-1}$ due to the symmetric stretching vibration of sulfonamide group (ν symmetric $SO_2$). By powder X-ray diffractometry using a powder X-ray diffractometer (Model SG-7, manufactured and sold by Rigaku Corporation, Japan; Target: Cu, Kv-mA: 30-10, Filter: Ni) (all of the measurements by powder X-ray diffractometry mentioned in the present specification are conducted using the same diffractometer), the anhydrous crystal of fasudil hydrochloride exhibits a diffraction pattern, in which diffraction angles (2 θ) are observed at approximately 14.7, 16.6, 17.5, 20.5, 24.6 and 25.5 (the range of error is ±0.2), and especially at approximately 17.5 and approximately 24.6, characteristic diffraction angles are observed.

Further, as shown in FIG. 2 of the accompanying drawings, in the thermal analysis (using a thermal analyser, Model TAS-200 manufactured and sold by Rigaku Corporation, Japan) (all of the thermal analyses mentioned in the present specification are conducted using the same analyser), the anhydrous crystal of 1-(5-isoquinolinesulfonyl)homopiperazine hydrochloride exhibits only an endothermic peak at 222.5° C. which is characteristic of the anhydrous crystal.

Since 1-(5-isoquinolinesulfonyl)homopiperazine hydrochloride has a peculiar taste (bitter taste), it is necessary for a tablet containing 1-(5-isoquinolinesulfonyl) homopiperazine hydrochloride to be film-coated. The tablet to be film-coated is required to have a satisfactory hardness. Accordingly, with respect to a tablet containing 1-(5-isoquinolinesulfonyl)homopiperazine hydrochloride, when the anhydrous crystal obtained by the prior art is used, a high compression pressure is required for obtaining a tablet having a satisfactory hardness. However, the higher the compression pressure, the less the dissolution of 1-(5- isoquinolinesulfonyl)homopiperazine hydrochloride from the tablet when the tablet is orally taken.

Therefore, when a pharmaceutical preparation (tablet) having a high content of 1-(5-isoquinolinesulfonyl)homopiperazine hydrochloride is produced using the anhydrous crystal thereof, for producing a tablet which has a sufficient hardness to be film-coated and is excellent in dissolution of 1-(5-isoquinolinesulfonyl)homopiperazine hydrochloride from the tablet, large amounts of excipient and disintegrant are required. As a result, the size of the tablet inevitably becomes large.

Further, the anhydrous crystal of 1-(5-isoquinolinesulfonyl)homopiperazine hydrochloride has a problem in that the water content thereof is unstable.

SUMMARY OF THE INVENTION

In this situation, the present inventors have made extensive and intensive studies for solving the above-mentioned problems of 1-(5-isoquinolinesulfonyl)homopiperazine hydrochloride. As a result, it has been unexpectedly found that there is a novel type crystal of 1-(5-isoquinolinesulfonyl)homopiperazine hydrochloride, as a crystal other than the above-mentioned anhydrous crystal, i.e., a 1-(5-isoquinolinesulfonyl)homopiperazine hydrochloride hydrate (hereinafter, frequently referred to simply as a "fasudil hydrochloride hydrate") which has excellent shapeability and tablettability.

The present invention has been completed, based on these findings.

Accordingly, it is an object of the present invention to provide a novel 1-(5-isoquinolinesulfonyl)homopiperazine hydrochloride hydrate having excellent shapeability and stability.

The foregoing and other objects, features and advantages of the present invention will be apparent from the following detailed description and appended claims taken in connection with the accompanying drawings.

DETAILED DESCRIPTION OF THE INVENTION

In one aspect of the present invention, there is provided a 1-(5-isoquinolinesulfonyl)homopiperazine hydrochloride hydrate having a water content of from 2.5 to 15.5% by weight represented by the following formula (I):

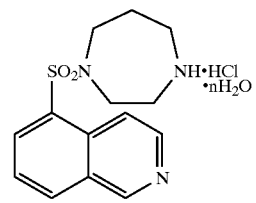

wherein n means a number in the range of from ½ to 3.

It has been found that, when 1-(5-isoquinolinesulfonyl)homopiperazine hydrochloride hydrate is trihydrate (fasudil hydrochloride trihydrate), the water content is from approximately 14.0 to approximately 15.5% by weight (the theoretical value calculated from the content of water of crystallization is 14.2% by weight).

Figure 3:
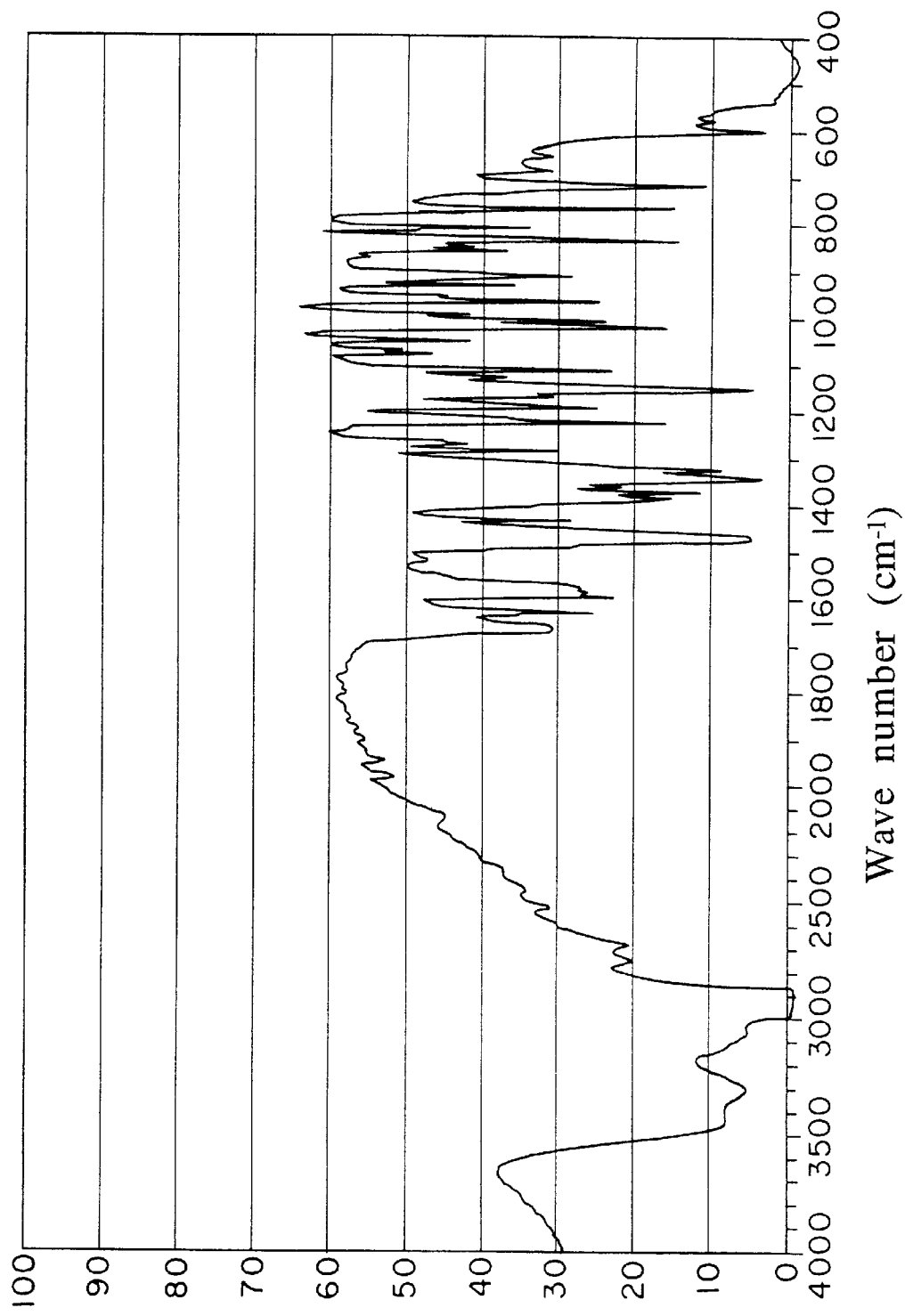
FIG. 3 is a chart showing the IR spectrum of the fasudil hydrochloride trihydrate obtained in Example 1.

The infrared absorption (IR) spectrum of the trihydrate, obtained using an infrared spectrometer, is shown in FIG. 3. The trihydrate exhibits, in the IR spectrum thereof, characteristic peaks, i.e., a peak at approximately 1630 cm$^{-1}$ due to the skeletal stretching vibration of an isoquinoline skeleton, (ν aromatic); a peak at approximately 1598 cm$^{-1}$ due to the skeletal stretching vibration of an isoquinoline skeleton, (ν aromatic); and a peak at approximately 1150 cm$^{-1}$ due to the symmetric stretching vibration of a sulfonamide group (ν symmetric SO$_2$), and the diffraction angles (2 θ) of the trihydrate as measured by powder X-ray diffractometry are observed at approximately 14.2, 16.3, 16.9, 23.1, 25.7 and 36.8, and especially, characteristic diffraction angles are observed at approximately 23.1 and approximately 36.8.

Figure 4:
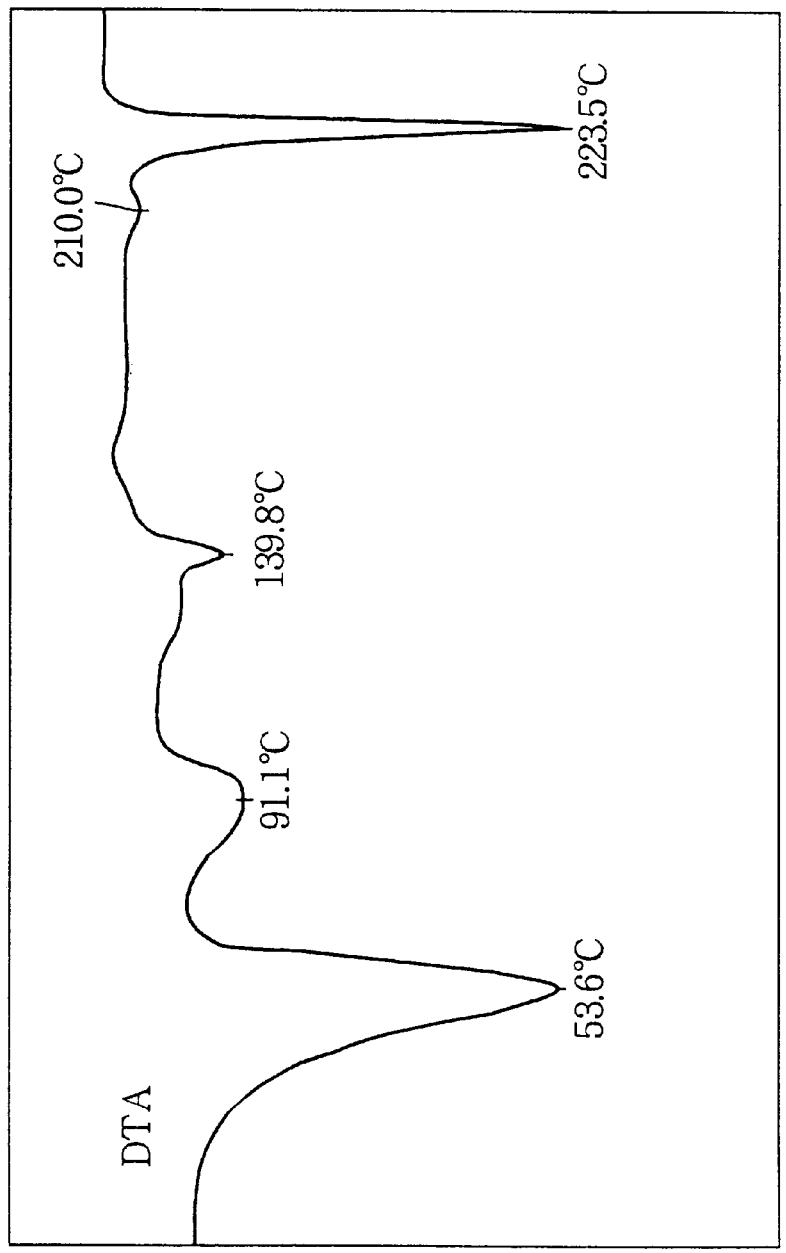
FIG. 4 is a chart showing the results of the thermal analysis of the fasudil hydrochloride trihydrate obtained in Example 1.

Further, as shown in FIG. 4, in the thermal analysis, 1-(5-isoquinolinesulfonyl)homopiperazine hydrochloride trihydrate exhibits endothermic peaks which are characteristic of the trihydrate.

The present inventors have made further studies, and found that, when fasudil hydrochloride trihydrate is left under conditions of a temperature of 40° C. and a relative humidity (RH) of 75%, the water content of fasudil hydrochloride trihydrate decreases with time from approximately 14.1% to at last approximately 2.8%–3.0%.

Therefore, fasudil hydrochloride trihydrate is required to be stored at a relative humidity of 90% or more. It is practically difficult to maintain the storage atmosphere at such a high humidity.

In this situation, the present inventors have made still further extensive and intensive studies with a view toward developing still another crystal of fasudil hydrochloride hydrate having more excellent stability during production and storage thereof. As a result, a novel crystal of 1-(5-isoquinolinesulfonyl)homopiperazine hydrochloride, as a crystal other than trihydrate (fasudil hydrochloride trihydrate), having satisfactory shapeability and stability, has been found. This novel crystal is 1-(5-isoquinolinesulfonyl)homopiperazine hydrochloride hemihydrate (fasudil hydrochloride hemihydrate) and it is so stable that the water content thereof does not change under conditions of a temperature of 40° C. and an RH of 75% for 96 hours. More specifically, fasudil hydrochloride hemihydrate has a water content of from approximately 2.5 to approximately 3.1% by weight (the theoretical value calculated from the content of water of crystallization is 2.67% by weight).

Figure 5:
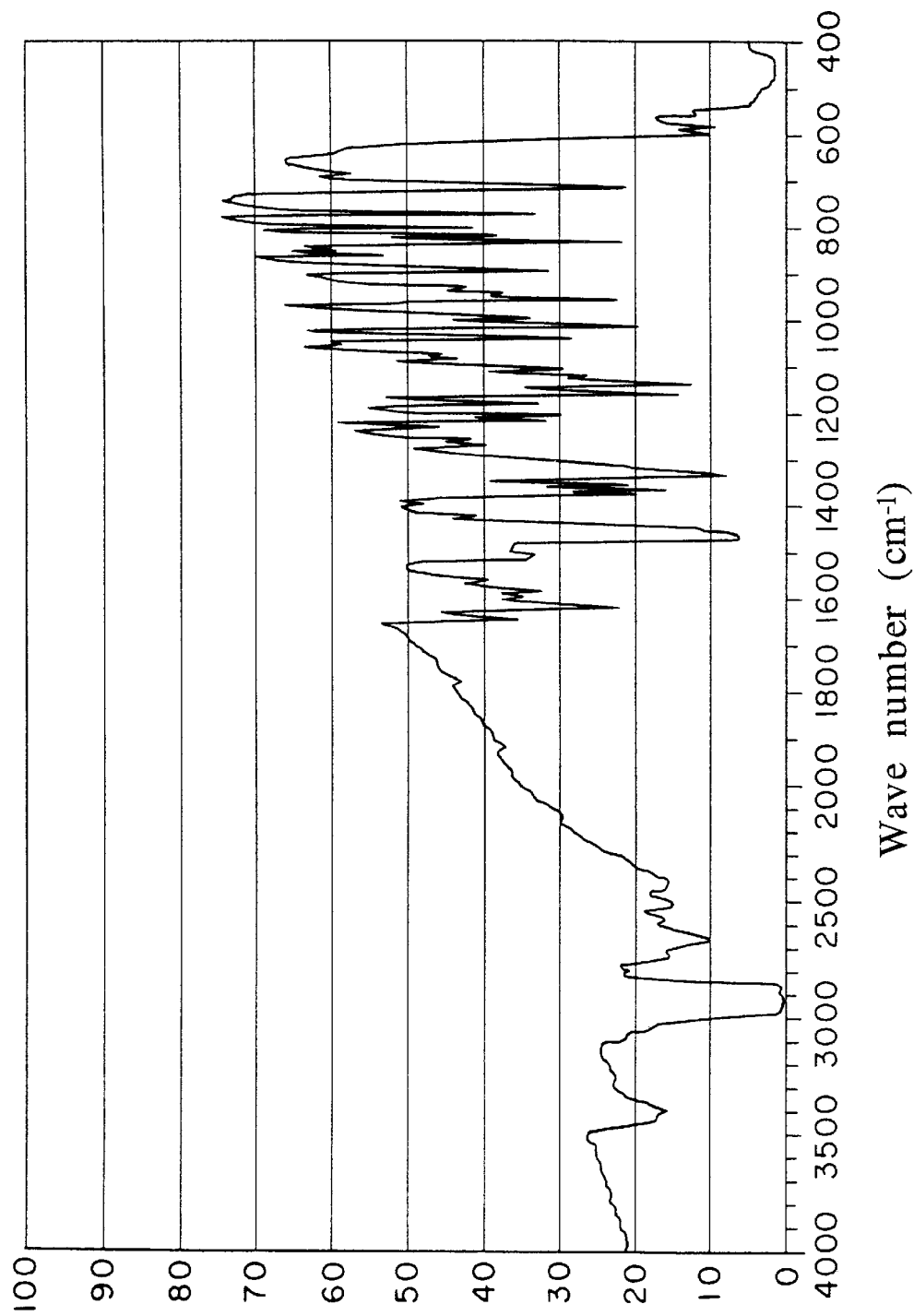
FIG. 5 is a chart showing the IR spectrum of the fasudil hydrochloride hemihydrate obtained in Example 3.

The IR spectrum of the hemihydrate, obtained using an infrared spectrometer, is shown in FIG. 5. The hemihydrate exhibits, in the IR spectrum thereof, characteristic peaks, i.e., a peak at approximately 1620 cm$^{-1}$ due to the skeletal stretching vibration of an isoquinoline skeleton, ($\nu$ aromatic); a peak at approximately 1592 cm$^{-1}$ due to the skeletal stretching vibration of an isoquinoline skeleton, ($\nu$ aromatic); and a peak at approximately 1140 cm$^{-1}$ due to the symmetric stretching vibration of a sulfonamide group ($\nu$ symmetric $SO_2$), and the diffraction angles (2 $\theta$) of the hemihydrate as measured by powder X-ray diffractometry are observed at approximately 8.4, 12.4, 14.0, 16.2, 16.8, 18.2, 19.5, 22.4 and 25.6, and especially, characteristic diffraction angles are observed at approximately 14.0 and approximately 18.2.

Figure 6:
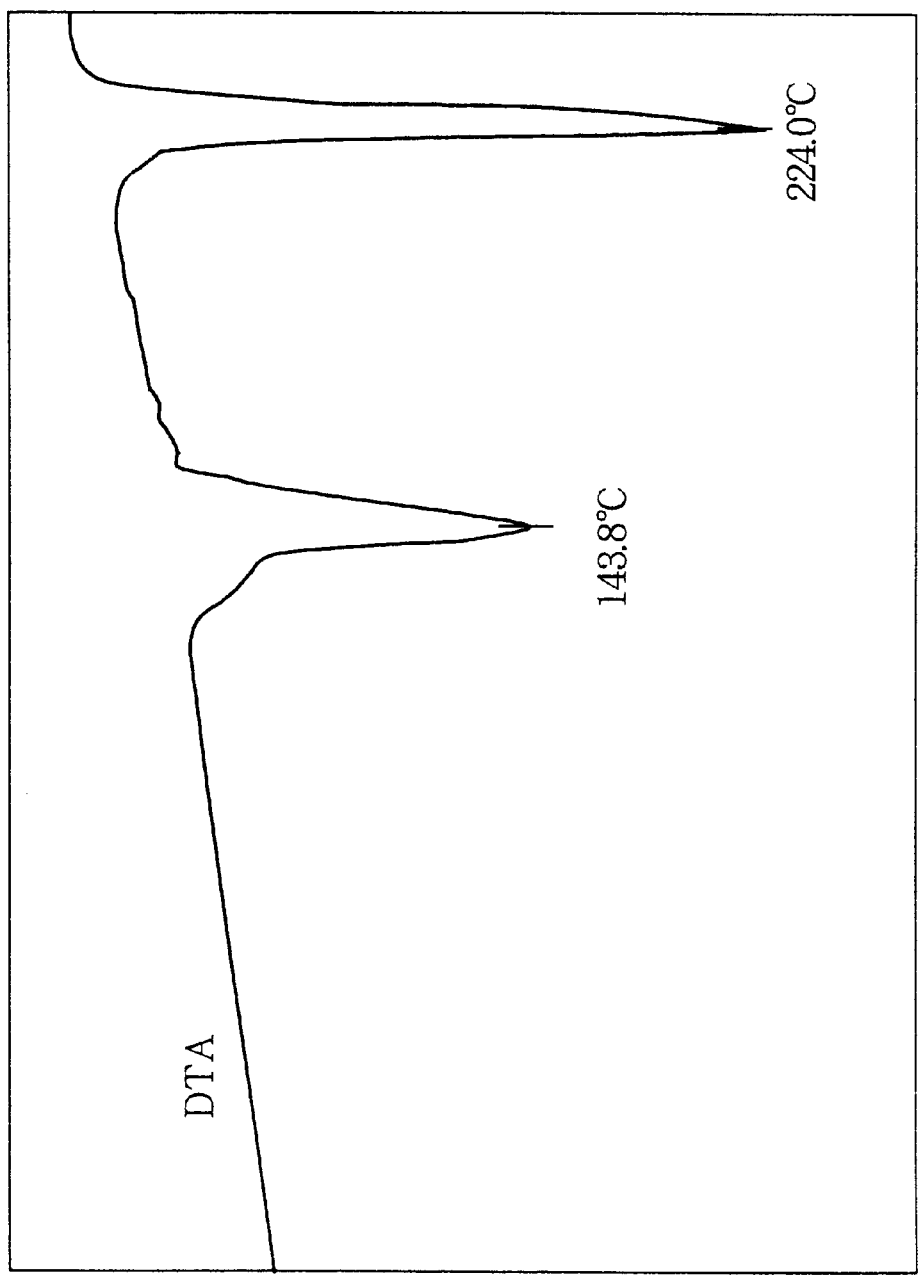
FIG. 6 is a chart showing the results of the thermal analysis of the fasudil hydrochloride hemihydrate obtained in Example 3.

Further, as shown in FIG. 6, in the thermal analysis, the fasudil hydrochloride hemihydrate exhibits endothermic peaks which are characteristic of the hemihydrate.

With respect to preferred examples of the hydrates of the present invention, there can be mentioned 1-(5-isoquinolinesulfonyl)homopiperazine hydrochloride hemihydrate (fasudil hydrochloride hemihydrate) having a water content of from approximately 2.5 to approximately 3.1% by weight, which corresponds to a compound of formula (I) wherein n is ½, and 1-(5-isoquinolinesulfonyl) homopiperazine hydrochloride trihydrate (fasudil hydrochloride trihydrate) having a water content of from approximately 14.0 to approximately 15.5% by weight, which corresponds to a compound of formula (I) wherein n is 3. Of these two types of hydrates, 1-(5-isoquinolinesulfonyl) homopiperazine hydrochloride hemihydrate (fasudil hydrochloride hemihydrate) is more preferred.

Further, preferred example of the above-mentioned fasudil hydrochloride hemihydrate is a hemihydrate which exhibits, in the IR spectrum thereof, characteristic peaks, i.e., a peak at approximately 1620 cm$^{-1}$ due to the skeletal stretching vibration of an isoquinoline skeleton, ($\nu$ aromatic); a peak at approximately 1592 cm$^{-1}$ due to the skeletal stretching vibration of an isoquinoline skeleton, ($\nu$ aromatic); and a peak at approximately 1140 cm$^{-1}$ due to the symmetric stretching vibration of a sulfonamide group ($\nu$ symmetric $SO_2$), and which exhibits characteristic diffraction angles (2 $\theta$), as measured by powder X-ray diffractometry, at approximately 14.0 and approximately 18.2.

With respect to the method for obtaining the crystal of 1-(5-isoquinolinesulfonyl)homopiperazine hydrochloride hydrate (fasudil hydrochloride hydrate) of the present invention, there is no particular limitation, but, for example, the following method can be mentioned. A crude anhydrous crystal of fasudil hydrochloride obtained by the synthesis method described in the above-mentioned prior art reference is dissolved in water heated to a temperature of from 40 to 80° C. to obtain an aqueous solution having a fasudil hydrochloride concentration of from 40 to 50%. The obtained solution is filtered with a membrane filter to obtain a filtrate, and the obtained filtrate is cooled to a temperature of from 0 to 5° C. and stirred at a temperature of from 0 to 5° C. for two days to thereby deposit a crystal. The resultant crystal is dried at a temperature of from 20 to 25° C. to thereby obtain fasudil hydrochloride trihydrate. Further, for example, the resultant crystal of fasudil hydrochloride trihydrate is dried at a temperature of from 40 to 70° C. for 2 to 100 hours to thereby obtain fasudil hydrochloride hemihydrate.

Further, a fasudil hydrochloride hydrate represented by formula (I) wherein n is larger than ½ and less than 3 can also be easily prepared by adjusting the conditions for drying the crystal of fasudil hydrochloride trihydrate.

A fasudil hydrochloride hydrate obtained by the above-mentioned method can be administered in the same manner as in the administration of the conventional fasudil hydrochloride anhydride.

The $LD_{50}$ value of fasudil hydrochloride hemihydrate determined by the acute toxicity test (oral administration) was from 280 to 285 mg/kg in mice (male) and from 345 to 360 mg/kg in rats (male). On the other hand, with respect to the pharmacological activity of fasudil hydrochloride hemihydrate, increases in blood flow in femoral and vertebral arteries of dog were measured. As a result, with a dose of 0.3 mg/kg (intravenous injection), the blood flow increased by 45% the femoral artery and 198% the vertebral artery, showing that fasudil hydrochloride hemihydrate has excellent pharmacological activity. Further, it has also been found that the pharmacological activity of fasudil hydrochloride trihydrate is substantially the same as that of fasudil hydrochloride hemihydrate.

BEST MODE FOR CARRYING OUT THE INVENTION

The present invention will be described in greater detail with reference to the following Examples, Reference Example and Comparative Example, which should not be construed as limiting the scope of the present invention.

Reference Example 1

40 liters of a chloroform solution containing 5.0 kg of 5-isoquinolinesulfonyl chloride was added dropwise to 40 liters of a chloroform solution containing 8.8 kg of homopiperazine over 1 hour while cooling with ice, to obtain a mixture. Subsequently, the obtained mixture was stirred for 1 hour while cooling with ice, to effect a reaction and then the resultant reaction mixture was subjected to extraction with a 2N aqueous solution of HCl, followed by separation of an aqueous phase. The aqueous phase was adjusted to a pH value of 10 with a 10% aqueous solution of NaOH to thereby obtain a solution having a pH value of 10. The obtained solution was subjected to extraction with 80 liters of chloroform, followed by separation of a chloroform phase. The resultant chloroform phase was washed with water and then dried over anhydrous sodium sulfate, and subsequently, the solvent was removed by distillation under reduced pressure to obtain a residue. The obtained residue was subjected to column chromatography using 150 kg of silica gel (Wakogel C-200, manufactured and sold by Wako Pure Chemical Industries, Ltd., Japan) and a mixed solvent of methanol and chloroform (5 v/v % methanol) as a developing solvent, and purified to obtain 6.01 kg of fasudil (yield 89%). The results of elemental analysis of fasudil: found (calculated) C: 57.59 (57.71), H: 5.92 (5.88), N: 14.29 (14.42), S: 10.83 (11.00) (wt %)

2.0 kg of fasudil was suspended in 10 liters of methanol to thereby obtain a suspension, and to the obtained suspension was added 10 liters of water and 6.57 liters of a 1N aqueous solution of HCl, followed by heating at 40° C. to dissolve fasudil to thereby obtain a solution. The obtained solution was evaporated to dryness under reduced pressure to thereby obtain a solid and then the obtained solid was recrystallized from 5 liters of a mixed solvent of water and methanol having a water/methanol ratio of 2/1 (v/v) to thereby obtain crystals and then the obtained crystals were dried at 120° C. for 8 hours. As a result, 2.01 kg of the anhydrous crystals of fasudil hydrochloride were obtained (yield: 89%).

The results of elemental analysis of fasudil hydrochloride anhydride: found (calculated) C: 51.01 (51.29), H: 5.47 (5.53), N: 12.80 (12.82), S: 10.14 (9.78), Cl: 10.53 (10.81)

Figure 1:
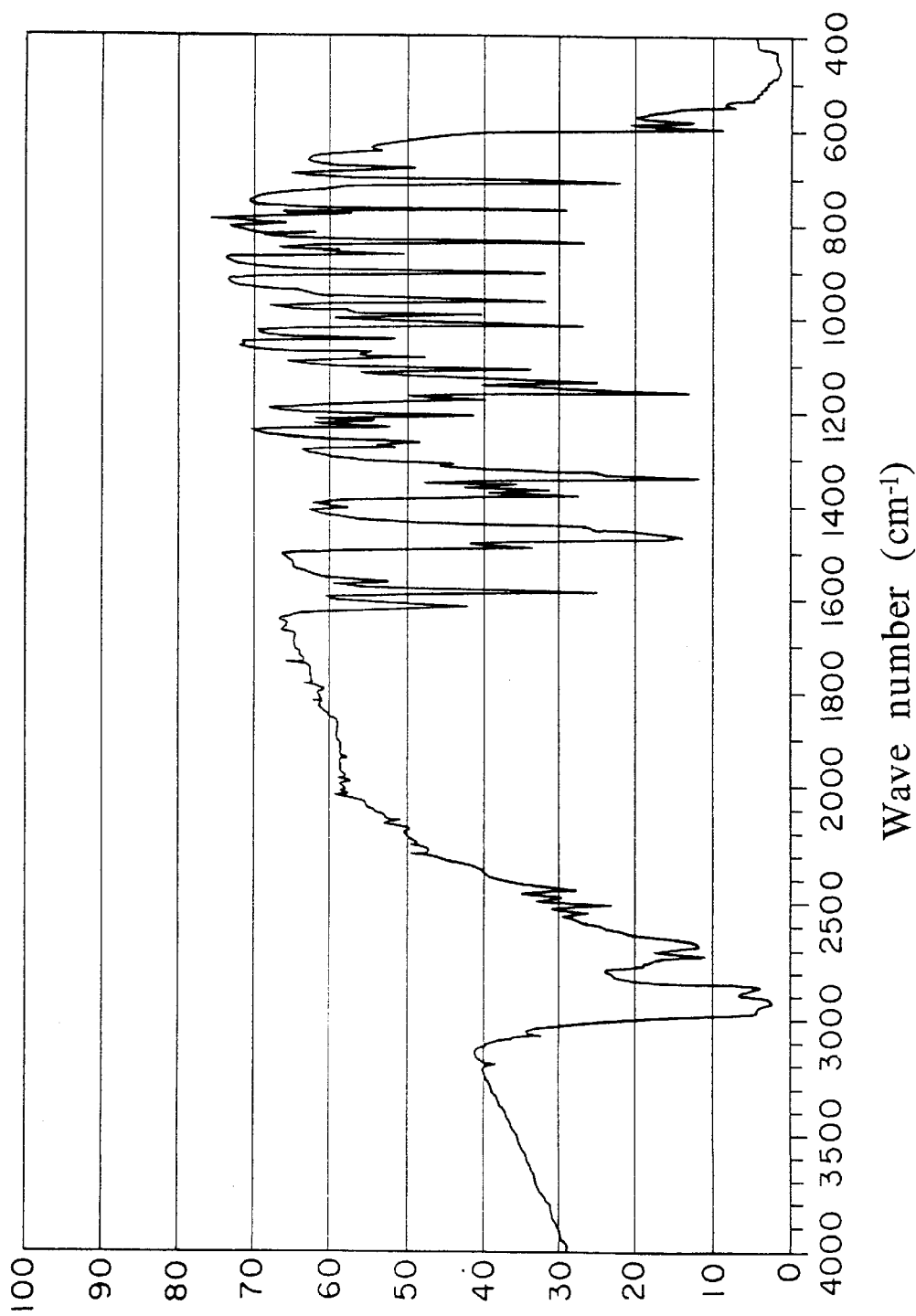
FIG. 1 is a chart showing the infrared absorption (IR) spectrum of the fasudil hydrochloride anhydride obtained in Reference Example 1.
Figure 2:
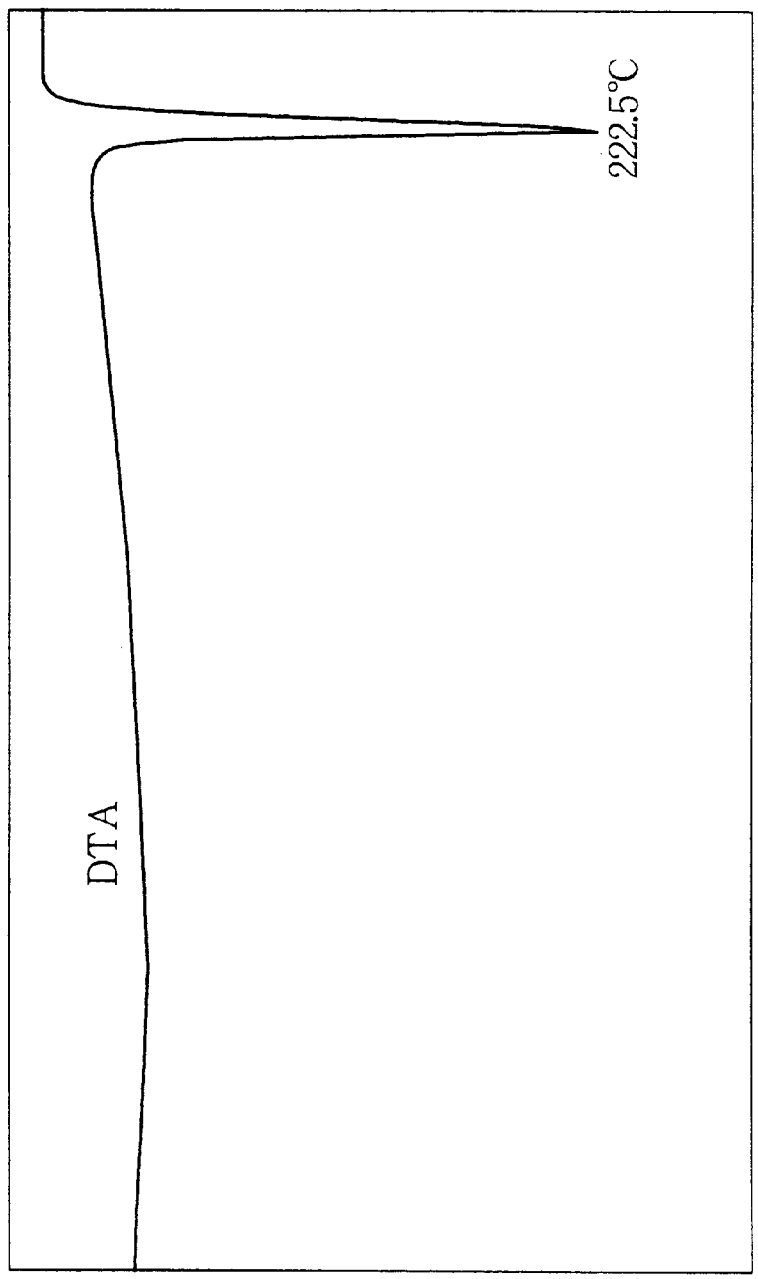
FIG. 2 is a chart showing the results of the thermal analysis of the fasudil hydrochloride anhydride obtained in Reference Example 1.

The water content of fasudil hydrochloride anhydride was 0.33%, and the infrared (IR) spectrum of fasudil hydrochloride anhydride is shown in FIG. 1. The diffraction angles (2 θ) of the anhydrous crystal as measured by powder X-ray diffractometry were observed at approximately 14.7, 16.6, 17.5, 20.5, 24.6 and 25.5. Further, as shown in FIG. 2, the results of the thermal analysis of the anhydrous crystals were characteristic of the anhydrous crystal.

EXAMPLE 1

210 g of fasudil hydrochloride anhydride obtained in Reference Example 1 above was dissolved in 525 ml of water heated to 50° C. and then the resultant solution was filtered with a membrane filter (pore size: 0.8 μm) to thereby obtain a filtrate, and the obtained filtrate was cooled to 5° C. and stirred at 5° C. for 48 hours to thereby deposit crystals. The crystals were collected by filtration under reduced pressure and dried at 25° C. for 6 hours, thereby obtaining 190 g of fasudil hydrochloride trihydrate (yield: 78%).

Fasudil hydrochloride trihydrate had a water content of from 14.0 to 15.5% as measured by the Karl Fischer method (theoretical value: 14.2%), and the IR spectrum of fasudil hydrochloride trihydrate is shown in FIG. 3. The diffraction angles (2 θ) of trihydrate as measured by powder X-ray diffractometry were observed at approximately 14.2, 16.3, 16.9, 23.1, 25.7 and 36.8. Further, as shown in FIG. 4, the results of the thermal analysis of trihydrate were characteristic of trihydrate.

EXAMPLE 2 AND COMPARATIVE EXAMPLE

Comparison of the shapeability of the fasudil hydrochloride trihydrate (trihydrate) obtained by the method described in Example 1 and that of the fasudil hydrochloride anhydride (anhydride) obtained by the method described in Reference Example 1 was made as follows.

The trihydrate and anhydride were individually fabricated into tablets under various compression pressure in Example 2 and Comparative Example, respectively. That is, 200 mg of each of the trihydrate and anhydride was individually, accurately weighed and fabricated into a tablet, by means of a handpress having a die and a punch having a concave of 12 R at a punching surface thereof and a diameter of 8 mm, under a compression pressure of from 400 to 1400 kg to thereby obtain a tablet. And then, each of the obtained tablets was individually subjected to a hardness test by means of hardness tester TS-50N (manufactured and sold by Okada Seiko Co. Ltd., Japan) to measure the hardness. The hardness of the tablet was defined as a load (unit: kg) such that the tablet was broken when loaded by means of a motor-driven weighting apparatus.

The results are shown in Table 1.

TABLE 1

(Hardness of tablet: kg)

| Compression pressure (kg) | Anhydrous crystal (Comparative Example) | | | Trihydrate | | |
|---|---|---|---|---|---|---|
| | Test No. 1 | Test No. 2 | Average of Test No. 1 and No. 2 | Test No. 1 | Test No. 2 | Average of Test No. 1 and No. 2 |
| 400 | 0.6 | 0.9 | 0.8 | 4.0 | 4.8 | 4.4 |
| 600 | 2.8 | 3.5 | 3.2 | 8.7 | 8.5 | 8.6 |
| 800 | 5.8 | 4.9 | 5.4 | 8.5 | 8.4 | 8.5 |
| 1,000 | 6.4 | 6.6 | 6.5 | 8.3 | 8.9 | 8.6 |
| 1,200 | 6.9 | 7.5 | 7.2 | 8.5 | 8.1 | 8.3 |
| 1,400 | 8.6 | 8.0 | 8.3 | 8.9 | 8.4 | 8.7 |

As is apparent from Table 1, with respect to the anhydride, the hardness of the tablet became high in accordance with the increase of the compression pressure. However, for obtaining a tablet having a hardness of 8 kg, the compression pressure was required to be as high as 1,400 kg. On the other hand, the hardness of the tablet of trihydrate became high under a low compression pressure as compared to that of the anhydride, thus showing that the trihydrate has excellent shapeability.

Therefore, it is apparent that the fasudil hydrochloride trihydrate is a crystal which has excellent shapeability and tablettability so that it is easy to be fabricated into tablets.

Further, since the fasudil hydrochloride trihydrate has excellent shapeability, the amounts of the excipient and disintegrant can be reduced, so that the size of the tablet can be reduced and the tablet becomes easy to be orally administered, even with a pharmaceutical preparation (tablet) having a high content of fasudil hydrochloride trihydrate.

However, as mentioned below, fasudil hydrochloride trihydrate has a problem of the stability, i.e., the change of water content thereof with time.

EXAMPLE 3

190 g of the fasudil hydrochloride trihydrate obtained by the method described in Example 1 was dried under conditions of a temperature of 40° C. and an RH of 75% for 10 hours to thereby obtain 167 g of fasudil hydrochloride hemihydrate (yield: 100%). The obtained fasudil hydrochloride hemihydrate had a water content of from 2.5 to 3.1% as measured by the Karl Fischer method (theoretical value: 2.67%) and the IR spectrum of fasudil hydrochloride hemihydrate is shown in FIG. 5. The diffraction angles (2 θ) of hemihydrate as measured by powder X-ray diffractometry were observed at approximately 8.4, 12.4, 14.0, 16.2, 16.8, 18.2, 19.5, 22.4 and 25.6. Further, as shown in FIG. 6, the results of the thermal analysis of hemihydrate were characteristic of hemihydrate.

EXAMPLE 4

20 g of each of the fasudil hydrochloride hemihydrate and fasudil hydrochloride trihydrate of the present invention was individually placed in a Petri dish and then, the Petri dishes were placed in a constant temperature-constant humidity chamber (manufactured and sold by TABAI ESPEC Corporation, Japan) maintained at 40° C. and 75% (RH) and left open. And then, the water content of each of the hydrates was at predetermined time intervals measured by means of the Karl Fischer apparatus and the change of the water content of each of the hydrates with time was recorded. Comparison between the stability of trihydrate and that of hemihydrate was made by measuring the change of the water content of each of the hydrates under the above-mentioned conditions.

Figure 7:
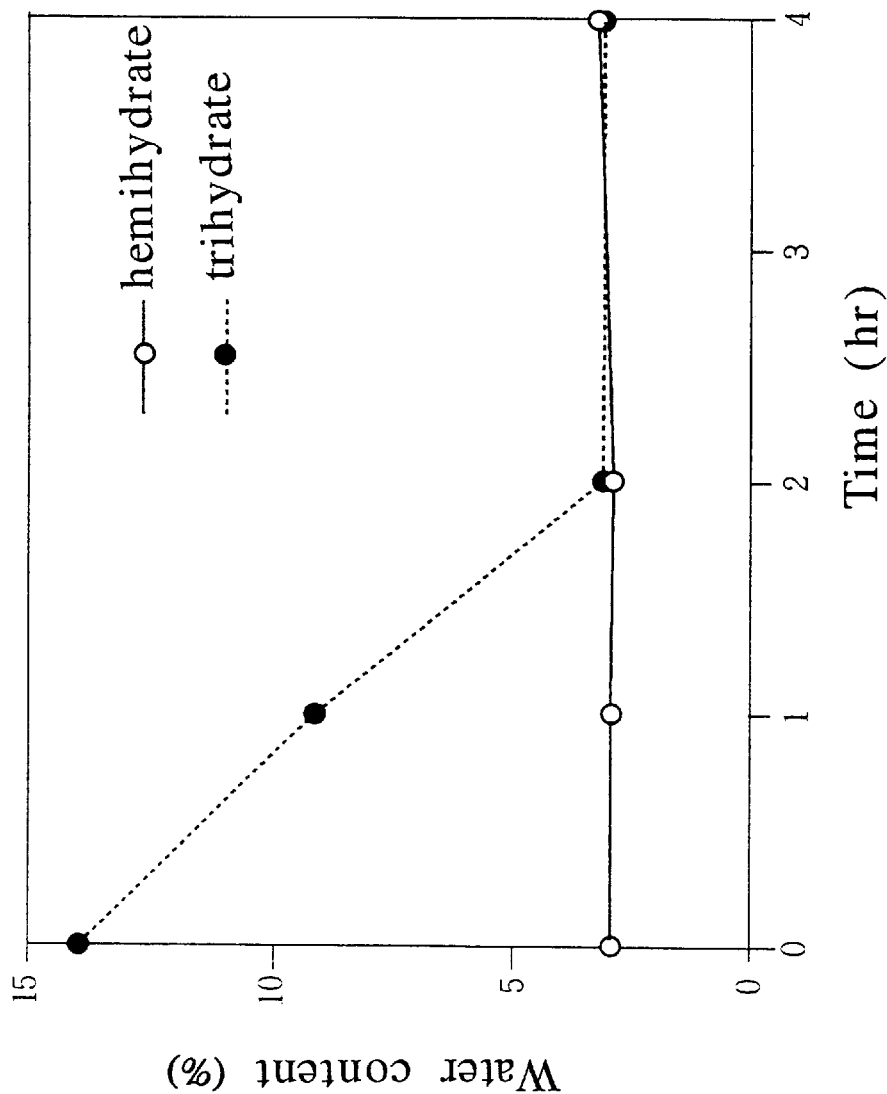
FIG. 7 is a chart showing the changes of the water contents of fasudil hydrochloride hemihydrate obtained in Example 3 and fasudil hydrochloride trihydrate obtained in Example 1 with time when the hydrates are left under conditions of a temperature of 40° C. and a relative humidity (RH) of 75%.

The results are shown in Table 2 and FIG. 7, wherein ●—● shows the case of trihydrate and ○—○ shows the case of hemihydrate.

TABLE 2

|  | Water content (%) of fasudil hydrochloride hemihydrate | Water content (%) of fasudil hydrochloride trihydrate |
| --- | --- | --- |
| 0 hour | 3.01% | 14.11% |
| 1 hour | 2.94% | 9.13% |
| 2 hours | 2.83% | 2.99% |
| 4 hours | 3.05% | 3.00% |

As shown in Table 2, with respect to the fasudil hydrochloride trihydrate, the water content decreased from 14.11 to 2.99%, showing that the fasudil hydrochloride trihydrate is not stable. In contrast, the water content of fasudil hydrochloride hemihydrate did not change, showing that the fasudil hydrochloride hemihydrate is stable. Further, the water content of fasudil hydrochloride hemihydrate did not change even after 96 hours under the above-mentioned conditions.

EXAMPLE 5

The fasudil hydrochloride hemihydrate (hemihydrate) obtained by the method described in Example 3 was fabricated into tablets under various compression pressures. That is, 200 mg of hemihydrate is accurately weighed and fabricated into a tablet, by means of a handpress having a die and a punch having a concave of 12 R at a punching surface thereof and a diameter of 8 mm, under a compression pressure of from 400 to 1400 kg to thereby obtain a tablet. And then, each of the obtained tablets was subjected to a hardness test by means of hardness tester TS-50N (manufactured and sold by Okada Seiko Co. Ltd., Japan) to measure the hardness, and comparison between the fasudil hydrochloride hemihydrate, fasudil hydrochloride trihydrate and fasudil hydrochloride anhydride was made with respect to the shapeability.

The results are shown in Table 3.

As is apparent from Table 3, the hardness of the tablet of the hemihydrate became high with a low compression pressure as compared to the anhydride, thus showing that the hemihydrate has excellent shapeability.

INDUSTRIAL APPLICABILITY

According to the present invention, there is provided a novel hydrate of 1-(5-isoquinolinesulfonyl)homopiperazine hydrochloride having excellent shapeability.

Since the 1-(5-isoquinolinesulfonyl)homopiperazine hydrochloride hydrate of the present invention has excellent shapeability as compared to a 1-(5-isoquinolinesulfonyl) homopiperazine hydrochloride anhydride, a tablet having satisfactory hardness can be obtained even with a relatively low compression pressure in a tableting process. Further, due to a reduction in the compression pressure needed for tableting, various advantages are brought about, such as improved disintegratability of the resultant tablet when the tablet is orally taken, so that good dissolution of 1-(5-isoquinolinesulfonyl)homopiperazine hydrochloride from the tablet can be achieved, as well as suppression of abrasion of a die and a punch in producing tablets by compression, and the like.

We claim:

1. A 1-(5-isoquinolinesulfonyl)homopiperazine hydrochloride hydrate represented by the following formula (I):

(I)

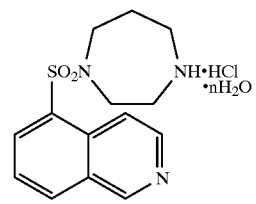

wherein n means a number in the range of from ½ to 3, said hydrate having a water content of from approximately 2.5 to approximately 15.5% by weight as measured by the Karl Fischer method.

2. The 1-(5-isoquinolinesulfonyl)homopiperazine hydrochloride hydrate according to claim 1, wherein n in formula (I) is ½, and the water content is from approximately 2.5 to approximately 3.1% by weight as measured by the Karl Fischer method.

TABLE 3

(Hardness of tablet: kg)

| | Anhydrous crystal (Comparative Example) | | | Trihydrate | | | Hemihydrate | | |
| --- | --- | --- | --- | --- | --- | --- | --- | --- | --- |
| Compression force | Test No. 1 | Test No. 2 | Average of Test No. 1 and No. 2 | Test No. 1 | Test No. 2 | Average of Test No. 1 and No. 2 | Test No. 1 | Test No. 2 | Average of Test No. 1 and No. 2 |
| 400 | 0.6 | 0.9 | 0.8 | 4.0 | 4.8 | 4.4 | 0.4 | 0.7 | 0.6 |
| 600 | 2.8 | 3.5 | 3.2 | 8.7 | 8.5 | 8.6 | 4.5 | 5.3 | 4.9 |
| 800 | 5.8 | 4.9 | 5.4 | 8.5 | 8.4 | 8.5 | 7.0 | 7.4 | 7.2 |
| 1,000 | 6.4 | 6.6 | 6.5 | 8.3 | 8.9 | 8.6 | 8.3 | 7.9 | 8.1 |
| 1,200 | 6.9 | 7.5 | 7.2 | 8.5 | 8.1 | 8.3 | 7.9 | 8.7 | 8.3 |
| 1,400 | 8.6 | 8.0 | 8.3 | 8.9 | 8.4 | 8.7 | 8.5 | 8.3 | 8.4 |

3. The 1-(5-isoquinolinesulfonyl)homopiperazine hydrochloride hydrate according to claim 1, wherein n in formula (I) is 3, and the water content is from 14.0 to approximately 15.5% by weight as measured by the Karl Fischer method.

4. A tablet comprising a compound of claim 1 as the active ingredient.

5. A tablet comprising a compound of claim 2 as the active ingredient.

6. A tablet comprising a compound of claim 3 as the active ingredient.

* * * * *